United States Patent
Toms

Patent Number: 6,036,660
Date of Patent: Mar. 14, 2000

[54] PATIENT MOVEMENT DETECTION

[75] Inventor: Martin Paul Toms, Waterlooville, United Kingdom

[73] Assignee: Pegasus Egerton Limited, Hampshire, United Kingdom

[21] Appl. No.: 08/997,729

[22] Filed: Dec. 24, 1997

[30] Foreign Application Priority Data

Dec. 24, 1996 [GB] United Kingdom .................... 9626860

[51] Int. Cl.[7] ........................................ A61B 1/06
[52] U.S. Cl. .................... 600/595; 600/534; 600/587; 600/595
[58] Field of Search .................... 600/534, 587, 600/595

[56] References Cited

U.S. PATENT DOCUMENTS

| | | |
|---|---|---|
| 3,727,606 | 4/1973 | Sielaff . |
| 5,448,996 | 9/1995 | Bellin et al. ............................ 600/534 |
| 5,515,865 | 5/1996 | Scanlon . |

FOREIGN PATENT DOCUMENTS

| | | |
|---|---|---|
| 476 138 | 3/1992 | European Pat. Off. . |
| 1261357 | 1/1972 | United Kingdom . |
| 1595417 | 8/1981 | United Kingdom . |
| 2 103 853 | 2/1983 | United Kingdom . |
| 2199953 | 7/1988 | United Kingdom . |
| WO 91/13575 | 9/1991 | WIPO . |

OTHER PUBLICATIONS

"The Prevention of Pressure Sores Significance of Spontaneous Bodily Movements," Exton–Smith et al, *The Lancet*, Sep. 18, 1991, pp. 1124–1127.

*Primary Examiner*—Max Hindenburg
*Attorney, Agent, or Firm*—Larson & Taylor

[57] ABSTRACT

For monitoring body movements of a patient on a support, particularly to ascertain risk of bed sores, at least one fluid filled cell is inserted between the patient and a support on which the patient is lying. There is a detector of fluctuations in the state of the fluid in the cell caused by body movements of the patient, providing an output dependent on the fluctuations. This output is analysed by discriminating between fluctuations which are indicative of major body movements and fluctuations which are indicative of minor body movements.

12 Claims, 5 Drawing Sheets

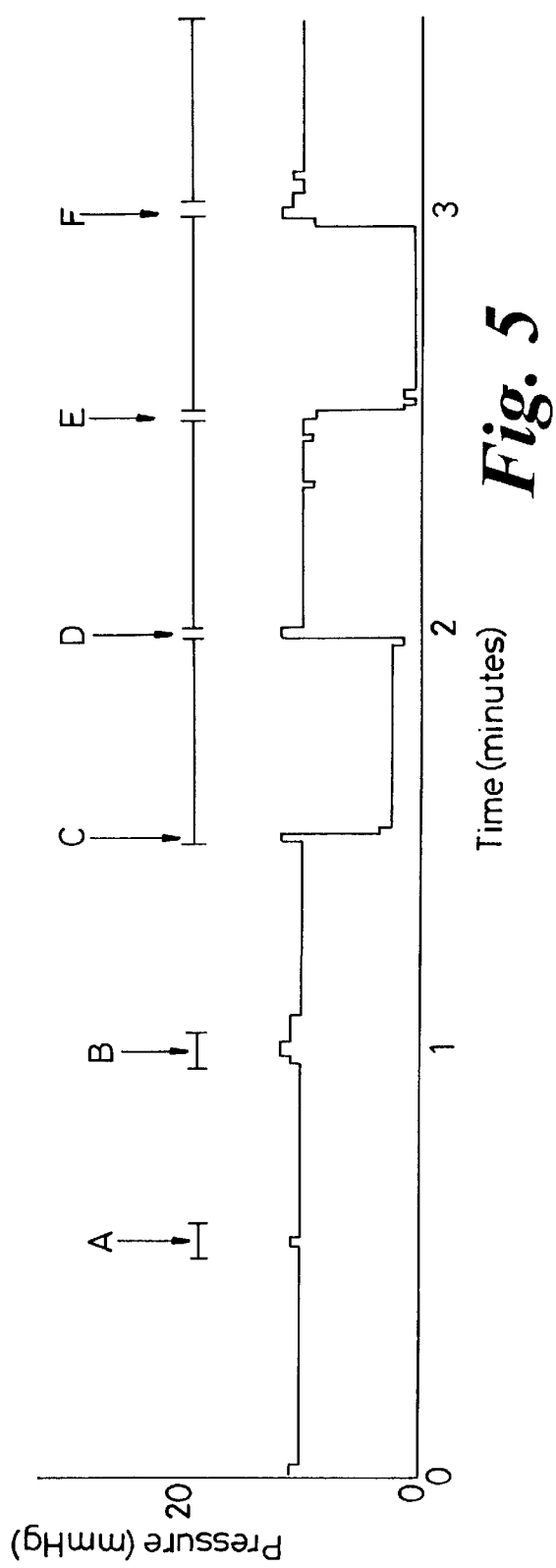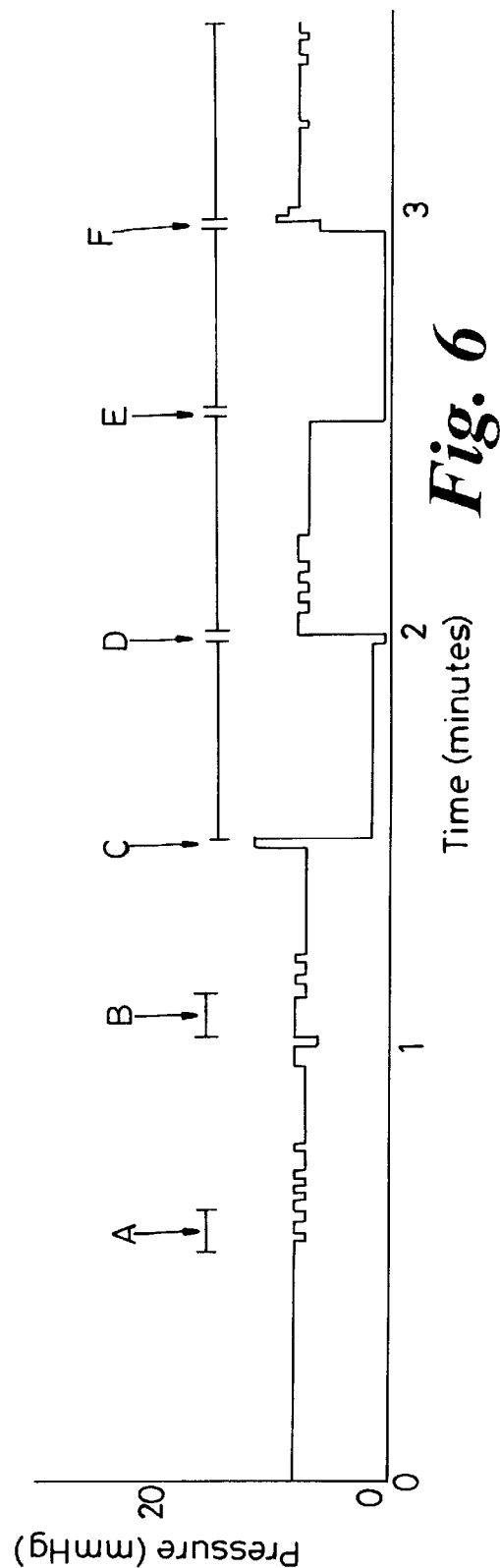

PATIENT MOVEMENT DETECTION

BACKGROUND OF THE INVENTION

1. Field of the Invention

The present invention relates to a device and a method for monitoring the body movements of a patient on a support.

2. Description of the Prior Art

Patients who spend long periods of time in bed are known to be at risk from developing pressure sores (tissue necrosis). To prevent this, regular turning of the patient is required, or a pressure relieving mattress, such as the Airwave™ sold by the applicants, may be used. The Airwave mattress is of the type illustrated in GB-A-1595417.

However in order to decide which form of mattress or what turning regime is required, it is necessary to assess the risk of individual patients for developing pressure sores. Studies carried out in 1961 by Exton-Smith and Sherwin (The Lancet, Nov. 18, 1961, pages 1124–1127) came to the conclusion that the risk of developing pressure sores is inversely related to the number or rate of spontaneous body movements. Exton-Smith and Sherwin counted body movements of patients using an inertial switch connected via a ratchet device to the mattress.

Attempts have been made to develop methods of monitoring spontaneous body movements. Watching is clearly not economically practical. Most efforts to date have been aimed at providing devices for attachment to legs of a bed frame which sense changes in the load on each leg of the bed frame, and/or changes in the centre of gravity of the bed frame. These changes can be related to patient movement, but the devices are bulky, expensive and difficult to install and remove from the bed.

Proposals have also been made for use of inflatable bodies on which a person is lying, in order to monitor body movement. Apnoea detection alarms for infants are proposed in U.S. Pat. No. 5,515,865, GB-A-1261357 and U.S. Pat. No. 3,727,606 which seek to monitor breathing by detecting pressure fluctuations within a mattress. U.S. Pat. No. 5,515,865 proposes among other things a pressure monitor connected to a water chamber. In GB-A-1261357 a heated wire sensor detects flows between mattress cells. In U.S. Pat. No. 3,727,606 a pressure sensor is attached to the mattress and is protected from large pressure changes caused by the infant's gross movements by a pop-off valve. These devices provide an alarm signal if no breathing movement is detected in a certain time period.

GB-A-2199953 discloses a device for measuring pressure at the interface between a patient's skin and a mattress, such as an alternating pressure mattress, to study the performance of the mattress. A small inflatable cell is placed at the interface location to be measured, and is periodically inflated by means of a compressor. The cell contains electrical contacts which break and make as the cell is inflated and deflated. By this method the interface pressure variation is plotted.

WO 91/13575 describes a mattress which monitors and records movements of a person lying on it. The mattress has many inflated cells in square arrays in four zones, at waist, hip, shoulder and foot, and a pressure-responsive readout device for each zone which reads out and records pressure changes resulting from movement of the patient as charts. It is suggested that from the charts of pressure fluctuations at these four zones, a doctor can diagnose sleep disorders, and it is described how in the charts breathing movements and arm and leg movements can be detected, within time zones in which the patient was lying on their back, side and front. The device is complex, and provides only a display of pressure changes as an output.

None of those devices provide an output which is related to the risk of development of pressure sores by a patient.

SUMMARY OF THE INVENTION

The object of the invention is to provide a device for monitoring body movements of a patient on a support which gives as an output data useful for assessing risk of development of pressure sores.

According to the invention in one aspect there is provided a device for monitoring body movements of a patient on a support, including:

at least one fluid filled cell insertable between a patient and a support on which the patient is supported;

means for detecting fluctuations in the state of the fluid in said at least one cell caused by body movements of the patient and providing an output dependent on said fluctuations; and means for analysing said output and providing an output dependent on the analysis, adapted and arranged to discriminate between said fluctuations which are indicative of major body movements and said fluctuations which are indicative of minor body movements.

According to the invention in another aspect there is provided a method of monitoring body movements of a patient supported by a support, by:

detecting fluctuations in the state of the fluid in at least one fluid-filled cell arranged between a patient and a support on which the patient is supported;

conducting an analysis of the detected fluctuations, so as to distinguish said fluctuations which are indicative of major body movements from said fluctuations which are indicative of minor body movements; and providing an output dependent on said analysis.

The present invention provides a convenient and simple device and method for monitoring patient movements, to provide output useful in assessing risk of pressure sores.

The invention is based on the surprising finding that the output of a detector of fluctuations, e.g. pressure fluctuations, in a cell can be readily analysed so as to distinguish large body movements, particularly body turning movements such as lying-on-side to lying-on-back, lying-on-front to lying-on-side, from relatively small body movements such as arm or leg movements. The analysed output of number or frequency or spacing of such large body movements can then be used to provide an output signal indicative of risk of pressure sores. Of course, the risk of pressure sores also depends on the condition of the individual patient, but the objective output relating to large body movements is of great value to nurses and doctors in charge of patients at risk of pressure sores.

It is not necessary in the practice of the present invention to monitor fluctuations in more than one cell. The cell or cells should be appropriately located relative to the patient to detect body movements. It has been found for example that substantial baseline shifts of pressure in such a cell are strongly correlated with the occurrence of large body movements, whereas minor body movements do not generally cause baseline shifts. This is illustrated below.

In the cell monitored, the fluid is preferably a gas, particularly air, but use of a liquid, and even a highly viscous liquid such as a gel, is feasible.

The cell can be a flexible-walled cell which has a preliminary inflation pressure, e.g. in the range 5 to 40 mmHg above ambient atmospheric, without a patient's weight applied to it. This cell is maintained sealed during monitoring.

Alternatively the cell whose pressure is sensed for monitoring may be a cell (or a group of cells) of an alternating pressure mattress or other alternating pressure device which is undergoing pressure cycling in its normal operation. In this case, the pressure fluctuations due to cycling must be filtered out or compensated for.

The monitored fluctuations in the state of the fluid may be, for example, changes in the pressure of the fluid, or movement of the fluid. These changes are caused by the patient moving. Examples of such detectors include a pressure transducer, and an airflow detector. An electrical output is preferable, for ease of handling in the analysis stage.

The means for analysing the detected fluctuations may typically be a combination of software and electronic hardware, such as a programmed PC. The analysis means is able to distinguish between major and minor body movements. In order to do this, the analysis means can compare the amplitude and duration of each fluctuation with pre-determined threshold values after filtering out signals due to external events e.g. cycling of the pressure of the cell (which may be done to reduce risk of pressure sores), temperature changes, opening of a door.

The means for analysis of the fluctuations may also compare the frequency of fluctuations due to major body movement (e.g. number of such fluctuations per unit time) against a pre-determined value or values in order to assess the risk of the patient developing pressure sores.

It is also preferable that means for displaying the results of the analysis of the fluctuations are present in the device. These means may directly indicate the level of risk of the patient developing pressure sores, and may take any suitable form, for example a numerical value or a simple arrangement of signal lights, each light representing a different level of risk of developing pressure sores.

The invention further consists in a device for monitoring body movements of a patient on a support, including:

at least one fluid filled cell insertable between a patient and a support on which the patient is supported;

means for detecting fluctuations in the state of the fluid in said at least one cell caused by body movements of the patient and providing an output dependent on said fluctuations; and means for analysing said output and providing an output dependent on the analysis, said output being an indication of risk of development of pressure sores in the patient.

In yet another aspect, the invention consists in a method of monitoring body movements of a patient supported by a support, by:

detecting fluctuations in the state of the fluid in at least one fluid-filled cell arranged between a patient and a support on which the patient is supported;

conducting an analysis of the detected fluctuations, and obtaining from said analysis an output indicative of risk of development of pressure sores in the patient.

BRIEF INTRODUCTION OF THE DRAWINGS

Embodiments of the present invention will now be described in detail by way of example with reference to the accompanying drawings in which:

FIG. 5 is a graph showing pressure against time of a different air cell of a device according to the present invention under the same test conditions as in the test illustrated in FIG. 4;

FIG. 6 is a graph showing pressure against time of the same air cell as in FIG. 5, but with a lower air pressure, under the same test conditions as the test illustrated in FIG. 4;

DESCRIPTION OF THE PREFERRED EMBODIMENTS

Figure 1:
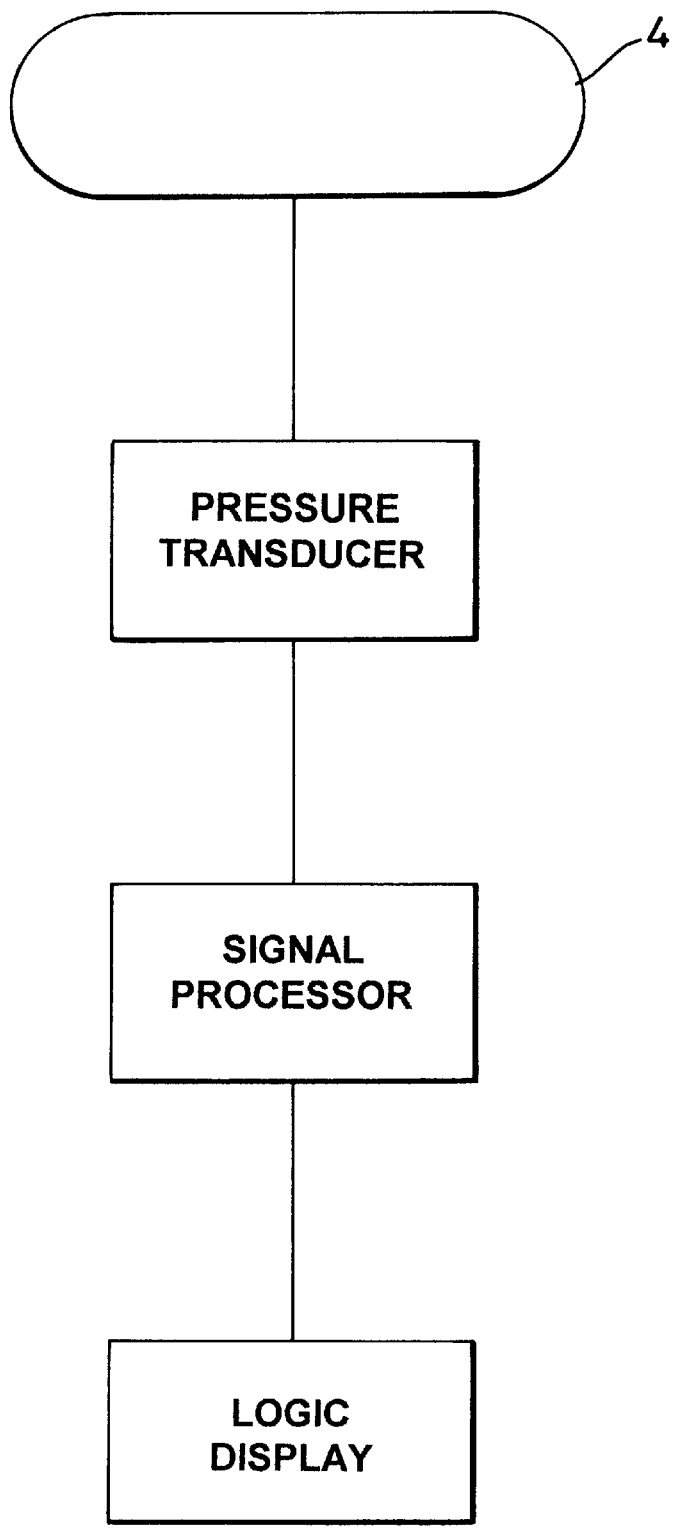
FIG. 1 is a functional block diagram of a device according to the present invention.
Figure 2:
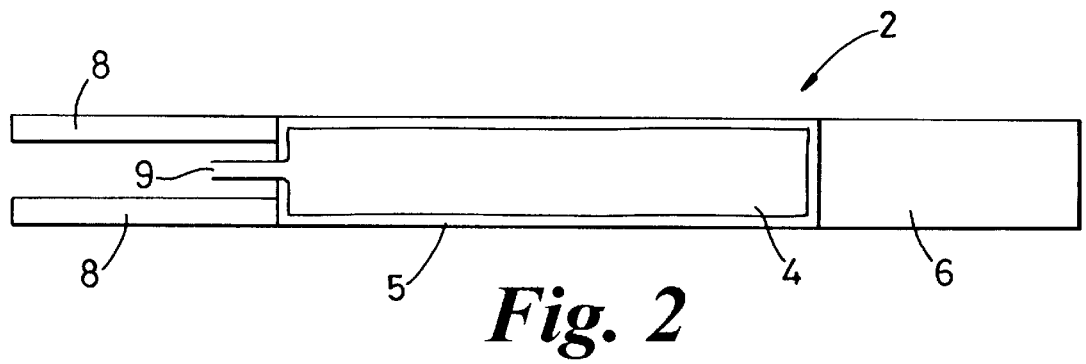
FIG. 2 is plan view of a low pressure air-filled cell as part of the device of FIG. 1 according to the present invention.

Referring to FIG. 1, this illustrates a device according to the present invention in terms of the functions of four parts: low pressure air chamber 4, pressure transducer, signal processor and logic display. FIG. 2 shows one possible low pressure air cell 2 which consists of a chamber 4 which is filled with air at a low pressure, e.g. 5 mmHg to 40 mmHg (0.67 kPa to 5.3 kPa). The chamber 4 is formed of two flexible air-impervious sheets joined at a RF welded seam 5 to form an air tight structure. When containing air, the structure is capable of being deformed by the application of weight and recovering to its normal dimensions when the weight is removed. The chamber is made out of plastics, for example polyurethane-coated nylon material and its dimensions are approximately 100 cm by 20 cm, i.e. substantially smaller than a mattress. Its thickness when inflated without load applied is approximately 1 to 2 cm. The dimensions are chosen so as to minimise any effect on the comfort of the patient. Thus it is preferred in the invention to use a cell having a length suitable to lie laterally under a patient, e.g. 0.5 to 1.5 m, a width of e.g. 3 to 60 cm, and a small height when inflated, e.g. 0.5 to 5 cm, but cells of larger height, e.g. up to 20 cm, may be monitored.

The cell 2 is held in place on a support, such as a mattress, by flap 6 and straps 8. The chamber has an air outlet 9 to a pressure transducer (not shown).

The pressure transducer (not shown) is electromechanical and constitutes the fluctuation detecting means. It measures variations in the internal air pressure of the air chamber 5. The transducer in this embodiment has a range 0 to 1 psi (0 to 55 mmHg, 0 to 7 kPa) and converts the air pressure into analogue electrical signals. It has external circuitry to provide temperature compensation and signal amplification. Such pressure transducers are commercially available.

The signal processor is the means for analysing the detected pressure fluctuations and is a combination of electronic hardware and software and may be e.g. a PC. This processor:

1) interrogates the signals from the pressure transducer to eliminate short signal durations of approximately less than 1 second that may be caused by minor, non-substantial, patient body movements or spurious pressure changes resulting from external sources other than the patient;

2) compares any signals of sufficient time duration to a reference signal which represents the pressure variation resulting from a major, or significant, patient movement and therefore give an indication of "VALID", or major, patient body movements;

3) counts the number of "VALID" patient body movements over a given period of time and generates a patient body movement rate; and 4) compares the actual patient movement body rate to a set of predefined movement rates relating to high, medium and low patient risks levels of developing pressure sores. These defined rates are derived from previous clinical research data.

The logic display is also a combination of electronic hardware and software and records the results of the signal processing function and provides the results on request via an appropriate man-machine interface, such as a series of lights, one for each level of risk of developing pressure sores.

Figure 3:
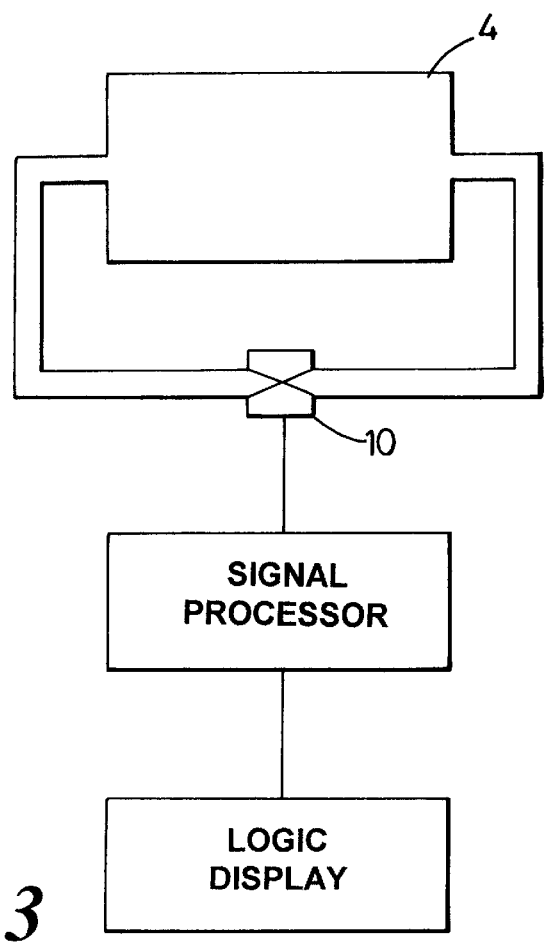
FIG. 3 is a functional block diagram of an alternative device according to the present invention.

An alternative embodiment of the present invention is illustrated by the functional block diagram of FIG. 3, where the sealed air chamber and pressure transducer have been replaced by a low pressure air cell that is connected in a circuit to an air flow sensor. The operation of the device is similar to that of the device of FIG. 1, except that changes in the air flow within the circuit are detected, rather than pressure fluctuations within the air cell.

Surprisingly it has been found that the fluctuations of the air pressure in the single inflated cell beneath the patient can be analysed to provide useful information about the patient's body movements. As the data discussed below shows, a major body movement, such as turning of the trunk, causes a baseline shift of the detected pressure in the cell, which can readily be distinguished from pressure fluctuations caused by minor body movements, since as raising an arm, or by other events. Similarly, air flows in the device of FIG. 3 can be analysed to distinguish between different types of body movement.

Figure 4:
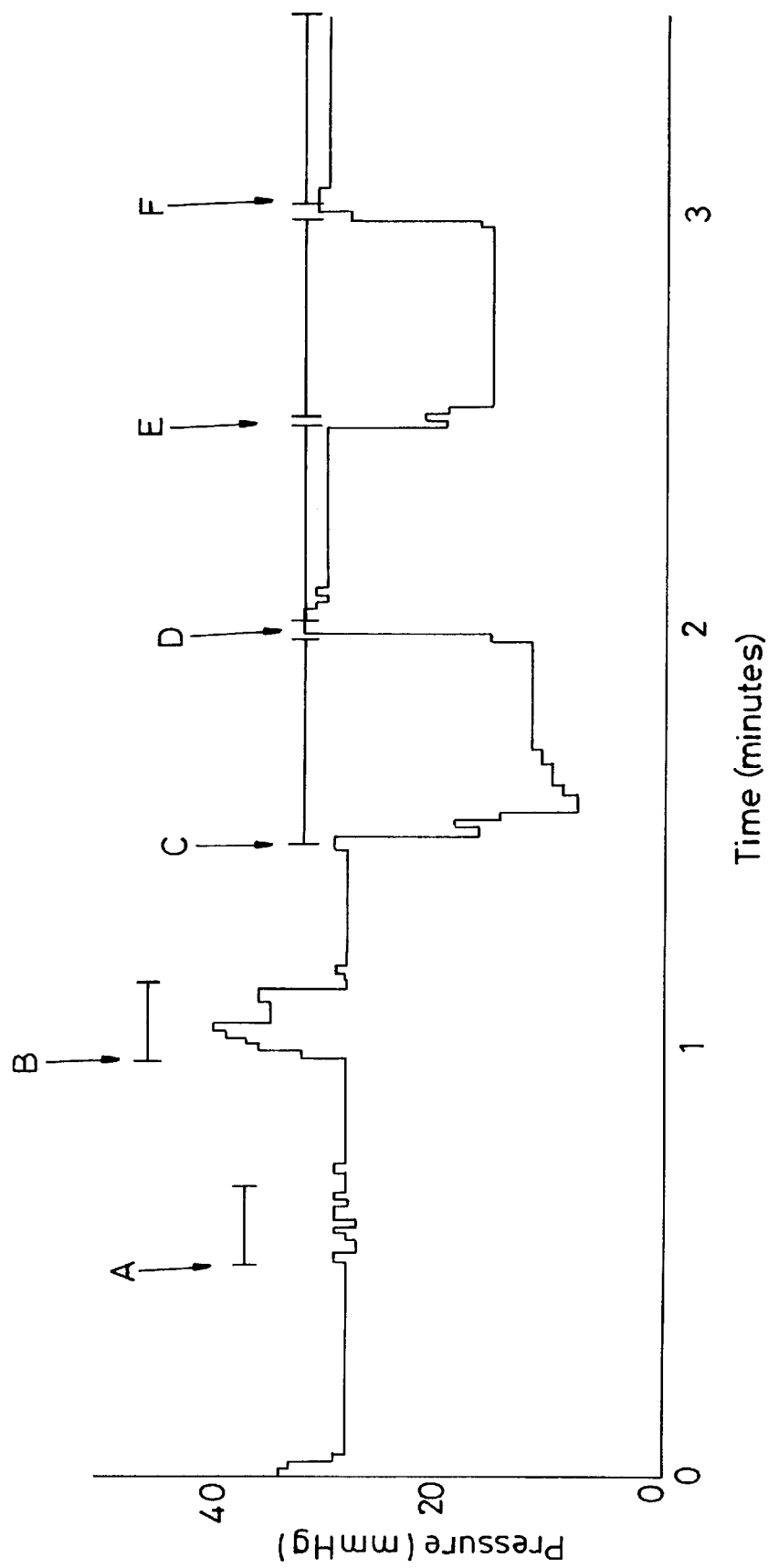
FIG. 4 is a graph showing pressure against time of an air cell of a device according to the present invention under test conditions with a volunteer person simulating a patient's spontaneous body movements.

FIGS. 4 to 8 are all graphs illustrating the effects of patient movements on the pressure of a low pressure air cell in the sacral area of a patient lying on a mattress. The patient movements were simulated by a real person on the mattress. In FIGS. 4 to 6 and 8, the patient followed a test regime as detailed below:

Movement A (t=30 s) Arm movement
Movement B (t=60 s) Leg movement
Movement C (t=90 s) Lateral movement to the right
Movement D (t=120 s) Return to supine position
Movement E (t=150 s) Lateral movement to the left
Movement F (t=180 s) Return to supine position FIG. 4 shows the test result when pressure was monitored in one of the three groups of cells of an Airwave™ alternating pressure mattress placed on a support. The Airwave mattress has an array of parallel elongate cells lying transversely to the longitudinal direction of the mattress and in two superimposed layers. They are subdivided into three groups, which are each cycled through a fixed inflation/deflation cycle in normal use. The pressure monitored was the pressure of the whole group of cells. For this test, all the cells were maintained inflated at an initial level of 30 mmHg (4 kPa), i.e. the groups of cells were not cycled through an inflation and deflation sequence, as in normal operation. The cell diameter is 10 cm. The lateral movements (C and E) each cause pressure changes of 15 mmHg (2.0 kPa) which are clearly distinguishable from the leg and arm movements (A and B respectively).

The air cell used in the test illustrated by FIGS. 5 to 8 had dimensions of 91.5 cm by 39.3 cm and was of the design shown in FIG. 2 and was placed on a standard hospital foam mattress.

In the test illustrated in FIGS. 5 and 6, the cell is simply placed between a patient and a standard hospital foam mattress. In the test of FIG. 5 the cell was at 10 mmHg (1.3 kPa) while in the test of FIG. 6 the pressure was reduced to 7 mmHg (0.9 kPa). Both of these tests show large baseline pressure changes, almost to 0 mmHg, at points C and E, corresponding to lateral movements, and only very small fluctuations at points A and B, which correspond to limb movements. The large difference in the size of the pressure changes makes it possible to distinguish between major and minor body movements.

Figure 7:
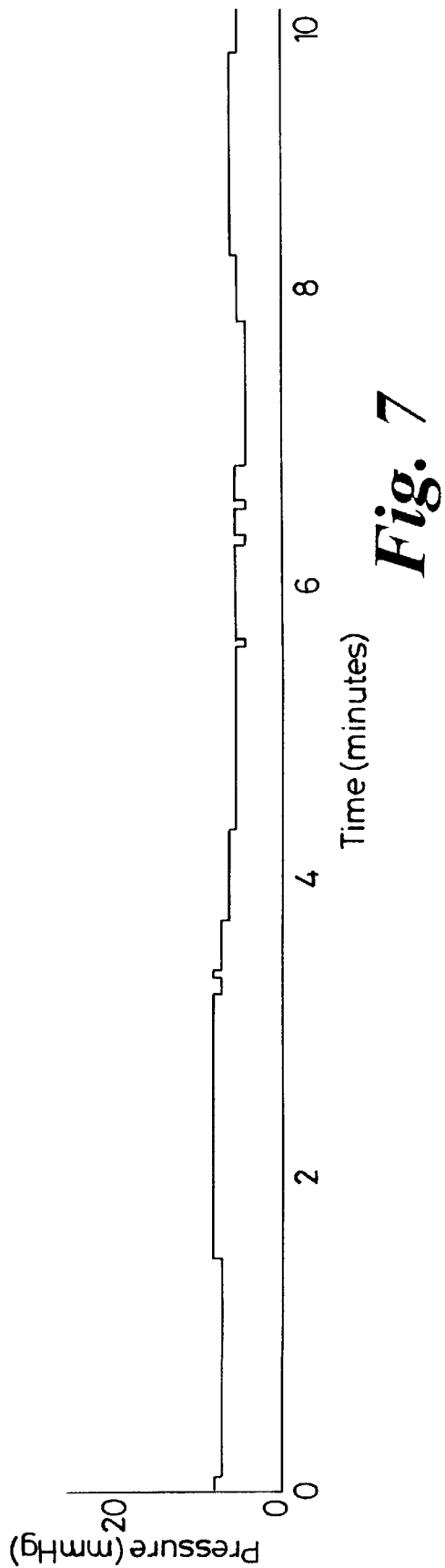
FIG. 7 is a graph showing pressure against time of an air cell of a device according to the present invention placed under a cover, where the patient is not moving.
Figure 8:
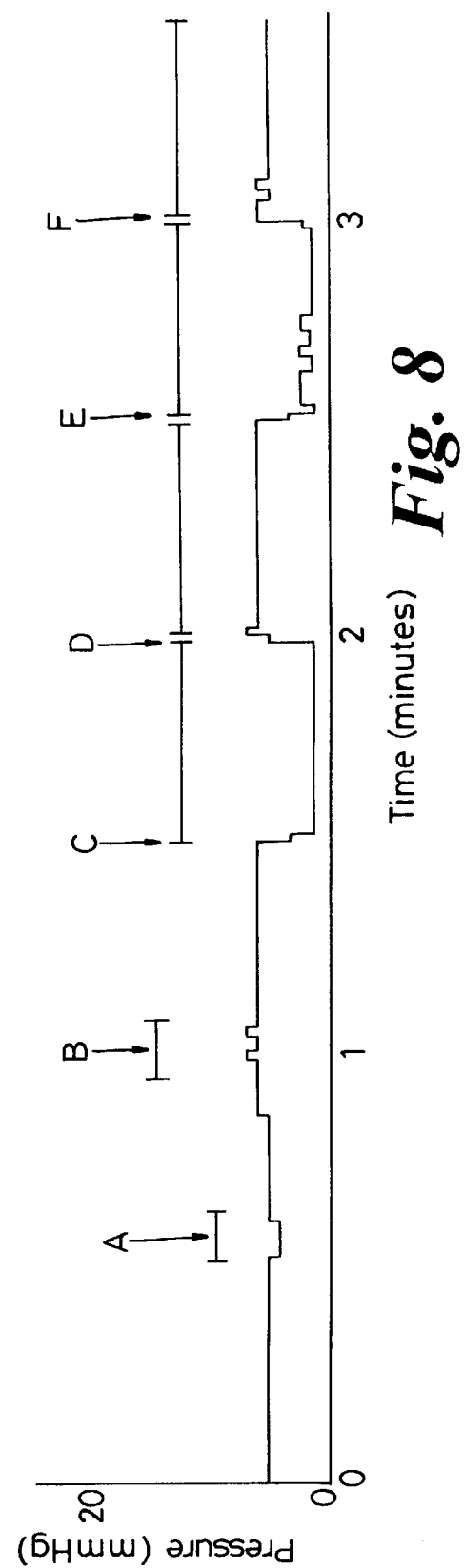
FIG. 8 is a graph showing pressure against time of the air cell arranged as in the test illustrated in FIG. 7, under the same test conditions as the test illustrated in FIG. 4.

In the tests of FIGS. 7 and 8 the air cell was placed between an Overture mattress (trade mark of the applicants denoting another marketed alternating cell inflatable mattress) and a standard hospital mattress. The test patient lay on the Overture. In the test of FIG. 7 the patient remained supine throughout and the graph shows small pressure variations, but no large fluctuations. In the test of FIG. 8, there was a cover sheet between the patient and the mattress. The pressure changes in FIG. 8 show that if the air cell is covered, there is little change in the sensitivity of the detector.

Although the above tests were carried out on air cells which had a fixed base pressure (or fixed amounts of air in them), the present invention can also be employed if the pressure in the air cell is cycling between two pressure values. This happens, for example, in the normal use of the Airwave™ mattress mentioned earlier. These mattresses include at least two groups of inflatable cells, which are cyclically inflated and deflated. The cycling of pressures in the groups of cells helps to reduce the risk of pressure sores. In these cases the signal processor can easily filter out the regular pressure cycling in order to detect the pressure fluctuations caused by the patient's body movements.

It should be understood that preferred embodiments of the present invention have been described above by way of example only and various alternative features or modifications from what has been described and illustrated can be made within the scope of the invention.

What is claimed is:

1. A device for monitoring body movements of a patient on a support, including:

at least one fluid filled cell insertable between a patient and a support on which the patient is supported;

means for detecting fluctuations in the state of the fluid in said at least one cell caused by body movements of the patient and providing an output dependent on said fluctuations; and means for analysing said output and providing an analysed output dependent on the analysis, adapted and arranged to effect discrimination between said fluctuations which are indicative of patient trunk turning movements and said fluctuations which are indicative of minor body movements in the form of arm or leg movement, and to provide said analysed output in dependence on said discrimination.

2. A device according to claim 1, further having means for displaying said analyzed output of the analysis of said fluctuations by said analysing means.

3. A device according to claim 1, further having means for deriving and displaying an indication of level of risk of pressure sores, said indication being derived by a comparison of the frequency of detected said patient body turning movements against at least one pre-determined value.

4. A device according to claim 1, wherein said analysing means discriminates between said patient trunk turning movements and said minor body movements by comparing at least one of the amplitude and duration of said fluctuations with at least one pre-determined threshold value.

5. A device according to claim 1, wherein said fluctuation detecting means detect one of pressure fluctuations of the fluid in the fluid-filled cell and movement of the fluid in the fluid-filled cell.

6. A method of monitoring body movements of a patient supported by a support, by:
   detecting fluctuations in the state of the fluid in at least one fluid-filled cell arranged between a patient and a support on which the patient is supported;
   conducting an analysis of the detected fluctuations, so as to distinguish said fluctuations which are indicative of patient trunk turning movements from said fluctuations which are indicative of minor body movements consisting of arm or leg movements; and
   providing an output dependent on said analysis.

7. A method according to claim 6, including displaying the results of the analysis of the fluctuations.

8. A method according to claim 6, wherein results of said analysis of the fluctuations are displayed in the form of an indication of level of risk of pressure sores, said indication arising from, in the step of analysing the fluctuations, comparing the frequency of said patient trunk turning movements against at least one pre-determined value.

9. A method according to claim 6, wherein said fluctuations detected are one of pressure fluctuations of the fluid in the fluid-filled cell and movements of the fluid in the fluid-filled cell.

10. A method according to claim 6, wherein the step of distinguishing between patient trunk turning movements and said minor body movements is carried out by comparing the amplitude and duration of said fluctuations with at least one pre-determined threshold value.

11. A device for monitoring body movements of a patient on a support, including:
   at least one fluid filled cell insertable between a patient and a support on which the patient is supported;
   means for detecting fluctuations in the state of the fluid in said at least one cell caused by body movements of the patient and providing an output dependent on said fluctuations; and
   means for analysing said output and providing an output dependent on the analysis, said output being an indication of risk of development of pressure sores in the patient.

12. A method of monitoring body movements of a patient supported by a support, by:
   detecting fluctuations in the state of the fluid in at least one fluid-filled cell arranged between a patient and a support on which the patient is supported;
   conducting an analysis of the detected fluctuations, and obtaining from said analysis an output indicative of risk of development of pressure sores in the patient.

* * * * *